United States Patent
Sakanishi et al.

(10) Patent No.: US 10,065,923 B2
(45) Date of Patent: Sep. 4, 2018

(54) THICKENING STABILIZER AND THICKENING STABILIZATION COMPOSITION USING SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Ohtake (JP); Takashi Saeki, Ube (JP); Mami Itoh, Ube (JP)

(73) Assignees: DAICEL CORPORATION, Osaka-Shi (JP); YAMAGUCHI UNIVERSITY, Yamaguchi-Shi (JP)

( * ) Notice: Subject to any disclaimer, the term of this patent is extended or adjusted under 35 U.S.C. 154(b) by 0 days.

(21) Appl. No.: 15/310,146

(22) PCT Filed: May 1, 2015

(86) PCT No.: PCT/JP2015/063103
§ 371 (c)(1),
(2) Date: Nov. 10, 2016

(87) PCT Pub. No.: WO2015/174300
PCT Pub. Date: Nov. 19, 2015

(65) Prior Publication Data
US 2017/0158619 A1 Jun. 8, 2017

(30) Foreign Application Priority Data
May 12, 2014 (JP) .................. 2014-098783

(51) Int. Cl.
| | | |
|---|---|---|
| C07C 233/58 | (2006.01) |
| C09K 8/035 | (2006.01) |
| A61K 8/42 | (2006.01) |
| A61K 8/37 | (2006.01) |
| A61Q 19/00 | (2006.01) |

(52) U.S. Cl.
CPC .............. *C07C 233/58* (2013.01); *A61K 8/37* (2013.01); *A61K 8/42* (2013.01); *A61Q 19/007* (2013.01); *C09K 8/035* (2013.01); *A61K 2800/48* (2013.01); *A61K 2800/52* (2013.01); *C07C 2101/14* (2013.01)

(58) Field of Classification Search
CPC ........ C09K 8/035; A61K 8/042; C07C 233/58

USPC ......... 564/153, 159; 507/153, 159, 131, 244
See application file for complete search history.

(56) References Cited

U.S. PATENT DOCUMENTS

| 2013/0085087 A1 | 4/2013 | Mesher et al. |
| 2014/0142004 A1 | 5/2014 | Mesher et al. |

FOREIGN PATENT DOCUMENTS

| JP | 1-163111 A | 6/1989 |
| JP | 10-273477 A | 10/1998 |
| JP | 2008-24614 A | 2/2008 |
| JP | 2009-155592 A | 7/2009 |
| WO | WO 2013/040718 A1 | 3/2013 |
| WO | WO 2014/043819 A1 | 3/2014 |

OTHER PUBLICATIONS

International Search Report, issued in PCT/JP2015/063103, PCT/ISA/210, dated Aug. 4, 2015.
Written Opinion of the International Searching Authority, issued in PCT/JP2015/063103, PCT/ISA/210, dated Aug. 4, 2015.

*Primary Examiner* — Venkataraman Balasubramanian
(74) *Attorney, Agent, or Firm* — Birch, Stewart, Kolasch & Birch, LLP

(57) ABSTRACT

A compound that thickens or gels a fluid organic substance to a desired viscosity or homogeneously stabilizes a composition containing a fluid organic substance, a thickening/stabilizing agent containing the compound, a thickened/stabilized composition containing the thickening/stabilizing agent and a fluid organic substance, and a method for producing a thickened/stabilized composition. The compound is represented by the following formula (1):

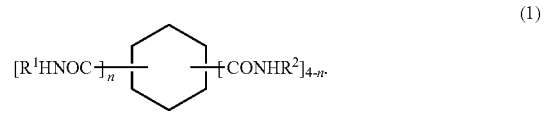

(1)

In the formula, $R^1$ and $R^2$ are different from each other and represent an aliphatic hydrocarbon group having not less than 4 carbon atoms, and n represents an integer of 1 to 3. The thickening/stabilizing agent of the present invention contains the compound.

9 Claims, No Drawings

THICKENING STABILIZER AND THICKENING STABILIZATION COMPOSITION USING SAME

TECHNICAL FIELD

The present invention relates to a novel compound having an effect of thickening/stabilizing a fluid organic substance such as an oil, a thickening/stabilizing agent using the same, and a thickened/stabilized composition containing the same. This application claims priority of Japanese Patent Application No. 2014-098783, filed on May 12, 2014, the entire contents of which are incorporated herein by reference.

BACKGROUND ART

A method for thickening/stabilizing a liquid is an industrially very significant technique, and for example, a mayonnaise, a salad dressing and the like that are emulsions in a metastable state can keep their emulsified states stably for a long period of time because their aqueous components are thickened and stabilized. Therefore, a variety of thickening stabilizers have been developed.

As a compound that thickens/stabilizes an aqueous medium, for example, alkyl acrylate copolymers and the like are known.

On the other hand, as a thickening/stabilizing agent for a fluid organic substance (for example, an organic substance having flowability such as an oil medium), 12-hydroxystearic acid is known (Patent Literature 1 and the like). 12-Hydroxystearic acid is mainly used in waste disposal of a cooking oil. When 12-hydroxystearic acid is used, however, a fluid organic substance can be induced to be either completely solidified or remained in the form of a liquid.

In addition, Patent Literature 2 describes, as a gelling agent for a hydrophilic or lipophilic compound, 1,2,3-propanetricarboxylic acid tris(2-methylcyclohexylamide).

CITATION LIST

Patent Literature

Patent Literature 1: Japanese Patent Laid-Open No. 01-163111
Patent Literature 2: Japanese Patent Laid-Open No. 2009-155592

SUMMARY OF INVENTION

Technical Problem

It has been found, however, that 1,2,3-propanetricarboxylic acid tris(2-methylcyclohexylamide) is difficult to dissolve in a fluid organic substance, and hence is difficult to be used as a thickener for a fluid organic substance.

Accordingly, an object of the present invention is to provide a compound that thickens or gels a fluid organic substance to a desired viscosity or homogeneously stabilized a composition containing a fluid organic substance.

Another object of the present invention is to provide a thickening/stabilizing agent containing the compound, a thickened/stabilized composition thickened, gelled or stabilized by the thickening/stabilizing agent, and a method for producing the same.

Solution to Problem

The present inventors made earnest studies to solve the above-described problems, resulting in finding the following: A compound represented by the following formula (1) can be easily dissolved in a fluid organic substance to thicken or gel the fluid organic substance, or homogeneously stabilize a composition containing the fluid organic substance (can stably retain a homogeneous state by preventing sedimentation, local aggregation or condensation of the composition), and if such a compound is selectively used in accordance with the type of the fluid organic substance, the fluid organic substance can be thickened or gelled to a desired viscosity or a composition containing the fluid organic substance can be homogeneously stabilized. The present invention was accomplished on the basis of these findings.

Specifically, the present invention provides a compound represented by the following formula (1):

[Formula 1]

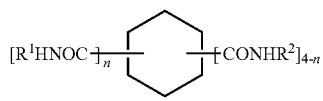

$$[R^1HNOC]_n \text{—} \bigcirc \text{—} [CONHR^2]_{4-n} \quad (1)$$

wherein $R^1$ and $R^2$ are different from each other and represent an aliphatic hydrocarbon group having not less than 4 carbon atoms, and n represents an integer of 1 to 3.

The present invention also provides a thickening/stabilizing agent containing the compound.

The present invention also provides a thickened/stabilized composition containing the thickening/stabilizing agent and a fluid organic substance.

The present invention also provides a method for producing a thickened/stabilized composition in which a thickened/stabilized composition is obtained through a step of compatibilizing the thickening/stabilizing agent and a fluid organic substance.

Specifically, the present invention relates to the following:

[1] A compound represented by the formula (1).

[2] The compound according to [1], in which the compound represented by the formula (1) is at least one compound selected from compounds represented by formulas (1-1) to (1-4).

[3] The compound according to [1] or [2], in which one of $R^1$ and $R^2$ of the formula represents a branched chain alkyl group having 6 to 10 carbon atoms, and the other represents a straight chain alkyl group or a straight chain alkenyl group having 12 to 18 carbon atoms.

[4] A thickening/stabilizing agent containing the compound according to any one of [1] to [3].

[5] The thickening/stabilizing agent according to [4], in which a content of the compound (or a total content of two or more compounds) represented by the formula (1) is not less than 60% by weight in a total amount of the thickening/stabilizing agent (100% by weight).

[6] A thickened/stabilized composition containing the thickening/stabilizing agent according to [4] or [5] and a fluid organic substance.

[7] The thickened/stabilized composition according to [6], in which the fluid organic substance is an organic substance having a viscosity, measured with a rheometer [a viscosity (η) at 25° C. and a shear velocity of 10 (l/s)], of less than 0.1 Pa·s.

[8] The thickened/stabilized composition according to [6] or [7], in which the fluid organic substance is at least one compound selected from a hydrocarbon oil, an ether, a halogenated hydrocarbon, a petroleum component, animal and vegetable oils, a silicone oil, an ester, an aromatic carboxylic acid and pyridine.

[9] A method for producing a thickened/stabilized composition, in which a thickened/stabilized composition is obtained through a step of compatibilizing the thickening/stabilizing agent according to [4] or [5] and a fluid organic substance.

[10] A method for producing a thickened/stabilized composition, in which a thickened/stabilized composition is obtained through a step of mixing and heating the thickening/stabilizing agent according to [4] or [5] and a fluid organic substance to be compatibilized, and then cooling the resultant.

Advantageous Effects of Invention

A compound of the present invention represented by the formula (1) can easily thicken or gel a fluid organic substance or homogeneously stabilize a composition containing a fluid organic substance when compatibilized with the fluid organic substance. Therefore, when the compound is used in a cosmetic product, a coating, food, a drug or the like, the viscosity of the resultant can be adjusted to a desired range, the constitution of the resultant can be homogeneously retained, and the usability of the resultant can be improved.

DESCRIPTION OF EMBODIMENTS

[Compound Represented by Formula (1)]

A compound of the present invention is represented by the following formula (1). In the formula, $R^1$ and $R^2$ are different from each other and represent an aliphatic hydrocarbon group having not less than 4 carbon atoms, and n represents an integer of 1 to 3.

[Formula 2]

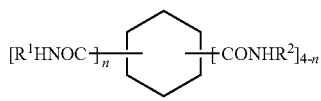

(1)

Examples of the compound represented by the formula (1) include compounds represented by the following formulas (1-1) to (1-4):

[Formula 3]

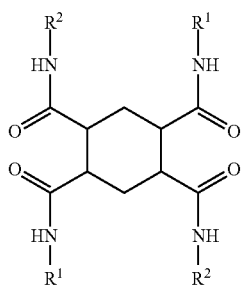

(1-1)

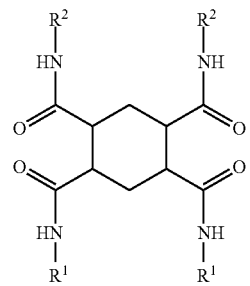

(1-2)

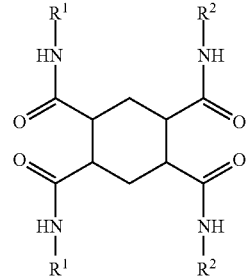

(1-3)

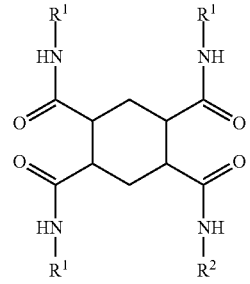

(1-4)

As the compound of the present invention represented by the formula (1), the compound represented by the formula (1-1) and/or (1-2) is particularly preferred because such a compound is excellent in solubility of a fluid organic substance. Such a compound is preferred also because it can impart pseudoplastic behavior and a high storage modulus to the fluid organic substance while keeping transparency if the fluid organic substance is transparent.

In the aforementioned formula, $R^1$ and $R^2$ are different from each other and represent an aliphatic hydrocarbon group having not less than 4 carbon atoms, and examples of such a group include straight chain or branched chain alkyl groups having about 4 to 20 (preferably 6 to 18, and particularly preferably 8 to 18) carbon atoms such as butyl, pentyl, isopentyl, hexyl, octyl, 2-ethylhexyl, decyl, lauryl, myristyl, stearyl and nonadecyl groups; straight chain or branched chain alkenyl groups having about 4 to 20 (preferably 6 to 18, and particularly preferably 12 to 18) carbon atoms such as 3-butenyl, 4-pentenyl, 2-hexenyl, 3-hexenyl, 4-hexenyl, 5-hexenyl, 7-octenyl, 9-decenyl, 11-dodecenyl and oleyl groups; and straight chain or branched chain alkynyl groups having about 4 to 20 (preferably 6 to 18, and particularly preferably 12 to 18) carbon atoms such as butynyl, pentynyl, hexynyl, octynyl, decynyl, pentadecynyl and octadecynyl groups.

As the compound of the present invention represented by the formula (1), a compound in which one of $R^1$ and $R^2$ represents a branched chain alkyl group having about 4 to 20 (preferably 4 to 18, more preferably 6 to 12, particularly preferably 6 to 10, and most preferably 8 to 10) carbon atoms and the other of $R^1$ and $R^2$ represents a straight chain alkyl group or straight chain alkenyl group having about 4 to 20 (preferably 6 to 20, more preferably 8 to 20, further preferably 10 to 20, particularly preferably 12 to 20, and most preferably 12 to 18) carbon atoms is particularly preferably used because such a compound is excellent in the solubility of a fluid organic substance and can exhibit an effect of thickening the fluid organic substance.

The compound represented by the formula (1) can be produced, for example, by any of the following methods and the like.

1. A method in which cyclohexanetetracarboxylic acid is reacted with thionyl chloride to obtain cyclohexanetetracarboxylic acid tetrachloride, and the thus obtained cyclohexanetetracarboxylic acid tetrachloride is reacted with an amine (1) ($R^1$—$NH_2$) and an amine (2) ($R^2$—$NH_2$) (wherein $R^1$ and $R^2$ are as defined above).

2. A method in which cyclohexanetetracarboxylic acid dianhydride is reacted with an amine (1) ($R^1$—$NH_2$) to obtain amic acid, which is condensed with an amine (2) ($R^2$—$NH_2$) using a condensing agent.

As the cyclohexanetetracarboxylic acid used in the production method 1, 1,2,4,5-cyclohexanetetracarboxylic acid can be suitably used.

Examples of the amines ($R^1$—$NH_2$ and $R^2$—$NH_2$) used in the production method 1 include amines having an aliphatic hydrocarbon group (such as straight chain or branched chain alkyl group, alkenyl group or alkynyl group) having not less than 4 carbon atoms (preferably 6 to 20 carbon atoms), such as butylamine, pentylamine, isopentylamine, hexylamine, octylamine, 2-ethylhexylamine, decylamine, laurylamine, myristylamine, stearylamine and oleylamine.

In the production method 1, the reaction between the cyclohexanetetracarboxylic acid tetrachloride and the amines can be performed, for example, by adding dropwise cyclohexanetetracarboxylic acid tetrachloride to a system charged with the amines.

The amount of the amines used (the sum of the amounts of the amine (1) and the amine (2) used) is, for example, about 4 to 8 moles, and preferably 4 to 6 moles per mole of the cyclohexanetetracarboxylic acid tetrachloride.

The ratio between the amine (1) and the amine (2) (former:latter, in molar ratio) to be used can be appropriately adjusted in accordance with a desired compound represented by the formula (1). In other words, the numbers of (—$CONHR^1$) groups and (—$CONHR^2$) groups contained in the resultant compound represented by the formula (1) can be controlled by adjusting the ratio between the amine (1) and the amine (2) to be used.

The reaction between the cyclohexanetetracarboxylic acid tetrachloride and the amines can be performed in the presence of or absence of a solvent. Examples of the solvent include saturated or unsaturated hydrocarbon solvents such as pentane, hexane, heptane, octane and petroleum ether; aromatic hydrocarbon solvents such as benzene, toluene and xylene; halogenated hydrocarbon solvents such as methylene chloride, chloroform, 1,2-dichloroethane, chlorobenzene and bromobenzene; ether solvents such as diethyl ether, diisopropyl ether, dibutyl ether, tetrahydrofuran, dioxane, 1,2-dimethoxyethane and cyclopentyl methyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oil. One of these can be used singly, or two or more of these can be used in combination.

The amount of the solvent used is, for example, about 50 to 300% by weight based on a total amount of the cyclohexanetetracarboxylic acid tetrachloride and the amines. If the amount of the solvent used exceeds the above-described range, a concentration of a reactive component tends to be lowered to lower the reaction rate.

The reaction (namely, the dropwise addition) between the cyclohexanetetracarboxylic acid tetrachloride and the amines is usually performed under normal pressure. An atmosphere of the reaction (namely, the dropwise addition) is not especially limited as long as the reaction is not impeded, and can be, for example, any of an air atmosphere, a nitrogen atmosphere, an argon atmosphere and the like. A reaction temperature (namely, a temperature employed in the dropwise addition) is, for example, about 30 to 60° C. A reaction time (namely, a time of the dropwise addition) is, for example, 0.5 to 20 hours. After completing the reaction (namely, the dropwise addition), an aging step may be performed. If the aging step is performed, an aging temperature is, for example, about 30 to 60° C., and an aging time is, for example, about 1 to 5 hours. The reaction can be performed by any of a batch method, a semi-batch method, a continuous method and the like.

After completing the reaction, the resultant reaction product can be separated/purified by, for example, separation means such as filtration, condensation, distillation, extraction, crystallization, adsorption, recrystallization or column chromatography, or separation means of a combination of any of these.

In the production method 2, for example, the cyclohexanetetracarboxylic acid dianhydride, the amine (1) ($R^1$—$NH_2$) and a solvent described below are put into and aged in a system to produce amic acid, and thereafter, the amine (2) ($R^2$—$NH_2$) and a condensing agent (such as carbodiimide or a salt thereof) are put into and aged in the resultant system to produce the compound represented by the formula (1).

As the cyclohexanetetracarboxylic acid dianhydride, 1,2,4,5-cyclohexanetetracarboxylic acid-1,2:4,5-dianhydride can be suitably used.

Examples of the amines (1) and (2) include those usable in the above-described production method 1.

The amount of the amine (1) used is, for example, about 2 to 4 moles, and preferably 2 to 3 moles per mole of the cyclohexanetetracarboxylic acid dianhydride. The amount of the amine (2) used is, for example, about 2 to 4 moles, and preferably 2 to 3 moles per mole of the cyclohexanetetracarboxylic acid dianhydride.

The carbodiimide is represented by the following formula:

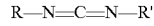

In this formula, examples of R and R' include a straight chain or branched chain alkyl group having 3 to 8 carbon atoms and a 3- to 8-membered cycloalkyl group, both of which optionally have a hetero atom-containing substituent. Here, R and R' may be the same or different. Besides, R and R' may be bonded to each other to form a ring together with (—N=C=N—) of the formula.

Examples of the straight chain or branched chain alkyl group having 3 to 8 carbon atoms include propyl, isopropyl, butyl, isobutyl, s-butyl, t-butyl, pentyl, isopentyl, s-pentyl, t-pentyl, hexyl, isohexyl, s-hexyl and t-hexyl groups.

Examples of the 3- to 8-membered cycloalkyl group include cyclopropyl, cyclobutyl, cyclopentyl, cyclohexyl and cyclooctyl groups.

Examples of the hetero atom-containing substituent include nitrogen atom-containing substituents like di-($C_{1-3}$) alkylamino groups such as an amino group and a dimethylamino group.

Examples of the carbodiimide include diisopropylcarbodiimide, dicyclohexyl-carbodiimide, and N-(3-dimethylaminopropyl)-N'-ethylcarbodiimide. Examples of the salt of carbodiimide include hydrochlorides (specifically, N-(3-dimethylaminopropyl)-N-ethylcarbodiimide hydrochloride and the like). One of these can be used singly, or two or more of these can be used in combination.

The amount of the carbodiimide used is, for example, about 2 to 6 moles, and preferably 2 to 4 moles per mole of the cyclohexanetetracarboxylic acid dianhydride.

As the solvent, proton accepting solvents (such as pyridine, triethylamine and tributylamine) excellent in the solubility of amic acid are preferably used. One of these can be used singly, or a mixture of two or more of these can be used.

The amount of the solvent used is, for example, about 50 to 300% by weight, and preferably 100 to 250% by weight based on a total amount of amic acid. If the amount of the solvent used exceeds the aforementioned range, the concentration of the reactive component tends to be lowered to lower the reaction rate.

The reaction is usually performed under normal pressure. An atmosphere of the reaction is not especially limited as long as the reaction is not impeded, and can be, for example, any of an air atmosphere, a nitrogen atmosphere, an argon atmosphere and the like. An aging temperature (a reaction temperature) is, for example, about 30 to 70° C. A time for aging the cyclohexanetetracarboxylic acid dianhydride and the amine is, for example, about 0.5 to 5 hours, and a time for aging amic acid and the amine is, for example, about 0.5 to 20 hours. The reaction can be performed by any of a batch method, a semi-batch method, a continuous method and the like.

After completing the reaction, the resultant reaction product can be separated/purified by, for example, separation means such as filtration, condensation, distillation, extraction, crystallization, adsorption, recrystallization or column chromatography, or separation means of a combination of any of these.

The compound represented by the formula (1) can form a fibrous self-assembly through self-association occurring through a hydrogen bond in an amide binding site. Besides, since the groups $R^1$ and $R^2$ have affinity with a fluid organic substance, when the compound is compatibilized with a fluid organic substance, it can thicken or gel the fluid organic substance, or homogeneously stabilize a composition containing the fluid organic substance. Furthermore, the compound represented by the formula (1) has appropriate crystallinity because the groups $R^1$ and $R^2$ are different from each other. Therefore, it can thicken/stabilize any fluid organic substance without limitation. In addition, if the fluid organic substance is transparent, it can thicken/stabilize the fluid organic substance with the transparency retained, so as to form a thickened/stabilized composition stable over time. Therefore, the compound is useful as a thickening/stabilizing agent (more specifically, a thickener, a gelling agent or a stabilizer) for a fluid organic substance. On the other hand, if the groups $R^1$ and $R^2$ in the compound represented by the formula (1) are the same group (namely, the compound represented by the formula (1) has the same four groups as a side chain), the crystallinity is so high that fluid organic substances that can be thickened/stabilized tend to be limited. Besides, the resultant becomes clouded through the thickening stabilization in many cases, which tends to impair the appearance. Moreover, the viscosity tends to be lowered over time.

[Thickening/Stabilizing Agent]

A thickening/stabilizing agent of the present invention contains one compound represented by the formula (1) alone or a combination of two or more thereof.

Herein, the term "thickening/stabilizing agent" means a compound that causes viscosity when dissolved in a fluid organic substance, and is used as a concept including a thickener imparting viscosity to a fluid organic substance, a gelling agent gelling a fluid organic substance, and a stabilizer increasing viscosity for homogeneously stabilizing a composition containing a fluid organic substance.

The thickening/stabilizing agent of the present invention may contain, in addition to the compound represented by the formula (1), an additional component (such as a base, a hydroxy fatty acid, an acrylic polymer, an oligomer ester such as a dextrin fatty acid ester, a particle of a metal oxide or the like) if necessary. A content of the additional component is such that the content of the compound (or the total content of two or more compounds) represented by the formula (1) in a total amount of the thickening/stabilizing agent (100% by weight) is, for example, not less than 0.5% by weight, preferably not less than 1% by weight, more preferably not less than 10% by weight, further preferably not less than 30% by weight, particularly preferably not less than 60% by weight, and most preferably not less than 85% by weight. Incidentally, the upper limit of the content of the compound represented by the formula (1) is 100% by weight. If the content of the compound represented by the formula (1) is out of the aforementioned range, it tends to be difficult to thicken or gel a fluid organic substance, or to homogeneously stabilize a composition containing a fluid organic substance.

As a form of the thickening/stabilizing agent of the present invention, any of various forms such as a powder, a granule, a liquid and an emulsion can be employed.

When the thickening/stabilizing agent of the present invention is compatibilized with a fluid organic substance (preferably, by mixing and heating to be compatibilized, and then cooling the resultant), the fluid organic substance can be thickened or gelled, and the fluid organic substance can be thickened or gelled so that the viscosity thereof can be increased by a factor of more than 1 and not more than 10000 (preferably a factor of 5 to 1000, and particularly preferably a factor of 10 to 1000) to a desired viscosity in accordance with use.

[Thickened/Stabilized Composition]

A thickened/stabilized composition of the present invention contains the above-described thickening/stabilizing agent and a fluid organic substance, and is a composition in which the fluid organic substance is thickened or gelled by the thickening/stabilizing agent or a homogeneously stabilized composition containing the fluid organic substance.

The thickened/stabilized composition can be produced through a step of compatibilizing the thickening/stabilizing agent and the fluid organic substance. More specifically, it can be produced by mixing the entire amount of the fluid organic substance and the thickening/stabilizing agent and heating the resultant to be compatibilized, and cooling the resultant. Alternatively, it can be produced by a method in which the thickening/stabilizing agent is mixed with a part of the fluid organic substance, the resultant is heated to be compatibilized and then cooled to produce a thickened/stabilized composition, and the remaining part of the fluid organic substance is added thereto.

The fluid organic substance used as a raw material is an organic substance having a viscosity, measured with a rheometer [a viscosity (η) at 25° C. and a shear velocity of 10 (1/s)], of less than 0.1 Pa·s, and examples include hydrocarbon oils (such as hexane, cyclohexane, isododecane, benzene, toluene, poly α-olefin and liquid paraffin), ethers (such as tetrahydrofuran), halogenated hydrocarbons (such as carbon tetrachloride and chlorobenzene), petroleum components (such as kerosene, gasoline, light oil and heavy oil), animal and vegetable oils (such as sunflower oil, olive oil, soybean oil, cone oil, castor oil, beef tallow, jojoba oil and squalane), silicone oils (such as dimethylpolysiloxane and methylphenylpolysiloxane), esters (such as octyldodecyl oleate, cetyl octanoate, cetyl ethylhexanoate, glyceryl tri-isooctanate and neopentyl glycol diisooctanate), an aromatic carboxylic acid and pyridine. One of these can be used singly, or two or more of these can be used in combination.

The amount of the thickening/stabilizing agent mixed (or used) depends upon the type of the fluid organic substance, and is for example, 0.1 to 100 parts by weight, preferably 0.5 to 90 parts by weight, particularly preferably 1 to 80 parts by weight, and most preferably 1 to 30 parts by weight based on 1000 parts by weight of the fluid organic substance. If the thickening/stabilizing agent is mixed (or used) in the above-described range, a composition in which the fluid organic substance is thickened or gelled or a composition having a homogeneously stabilized constitution can be obtained.

The thickened/stabilized composition of the present invention may contain, in addition to the thickening/stabilizing agent and a fluid organic substance, an additional component as long as the effects of the present invention are not impaired. Examples of the additional component include general compounds (such as a medicinal component, a pigment and a perfume) contained in a composition desired to be thickened/stabilized, such as a cosmetic product, a coating, food or a drug.

A temperature at the time of the compatibilization is appropriately selected in accordance with the types of the thickening/stabilizing agent and the fluid organic substance to be used, is not especially limited as long as the thickening/stabilizing agent and the fluid organic substance are compatible with each other at the temperature, and is preferably not more than 100° C., and is preferably in the vicinity of a boiling point of the fluid organic substance if the boiling point is not more than 100° C.

The cooling performed after the compatibilization may be gradually performed at room temperature or rapidly performed with ice cooling or the like as long as the resultant composition can be cooled to not more than room temperature (for example, 25° C.)

The viscosity measured with a rheometer [a viscosity (η) at 25° C. and a shear velocity of 10 (1/s)] of the thickened/stabilized composition of the present invention can be appropriately adjusted in accordance with use within a range of more than 1 and not more than 10000 times (preferably 5 to 1000 times, and particularly preferably 10 to 1000 times) of the viscosity of the fluid organic substance used as the raw material.

The thickened/stabilized composition of the present invention is not especially limited as long as it contains a fluid organic substance and is desired to be thickened/stabilized, and examples of such a composition include cosmetic products, coatings, food and drugs.

EXAMPLES

The present invention will now be more specifically described with reference to examples, and it is noted that the present invention is not limited to these examples.

Example 1 [Synthesis of Thickening/Stabilizing Agent (1) (1,2,4,5-cyclohexanetetracarboxylic Acid di(2-ethylhexylamide) di(oleylamide))]

A 100 mL four-necked separable flask equipped with a Dimroth condenser, a nitrogen inlet, a dropping funnel and a thermocouple was charged with 20 mL of pyridine, 4.5 g (0.02 mol) of 1,2,4,5-cyclohexanetetracarboxylic acid-1,2:4,5-dianhydride, and 10.6 g (0.04 mol) of oleylamine, and the resultant was aged for 3 hours with a temperature within the system set to 50° C.

Thereafter, 5.2 g (0.04 mol) of 2-ethylhexylamine and 5.5 g (0.044 mol) of diisopropylcarbodiimide were added thereto, and the resultant was aged for another 8 hours.

Then, a low-boiling component of the thus obtained crude liquid was removed with an evaporator, and the resultant was washed with methanol to obtain a pale yellow wet powder. The obtained wet powder was recrystallized with $CHCl_3/CH_3OH$ (70/30 (v/v)) to obtain 11.9 g of 1,2,4,5-cyclohexanetetracarboxylic acid di(2-ethylhexylamide) di(oleylamide) [a mixture of 1,2,4,5-cyclohexanetetracarboxylic acid-1,4-di(2-ethylhexylamide)-2,5-di(oleylamide) and 1,2,4,5-cyclohexanetetracarboxylic acid-1,5-di(2-ethylhexylamide)-2,4-di(oleylamide)] (yield: 61%). The structure of the thus obtained reaction product was analyzed by $^1$H-NMR. $^1$H-NMR (270 MHz, $CDCl_3$): δ0.81-0.88 (m, 18H), 1.0-1.4 (m, 68H), 1.40-1.45 (m, 2H), 1.76-1.99 (m, 8H), 2.50-3.10 (m, 8H), 3.30-3.45 (m, 4H), 5.21-5.40 (m, 4H), 6.31 (s, 4H)

Example 2 [Synthesis of Thickening/Stabilizing Agent (2) (1,2,4,5-cyclohexanetetracarboxylic Acid di(2-ethylhexylamide) di(stearylamide))]

A 100 mL four-necked separable flask equipped with a Dimroth condenser, a nitrogen inlet, a dropping funnel and a thermocouple was charged with 20 mL of pyridine, 4.5 g (0.02 mol) of 1,2,4,5-cyclohexanetetracarboxylic acid-1,2:4,5-dianhydride, and 10.7 g (0.04 mol) of stearylamine, and the resultant was aged for 3 hours with a temperature within the system set to 50° C.

Thereafter, 5.2 g (0.04 mol) of 2-ethylhexylamine and 5.5 g (0.044 mol) of diisopropylcarbodiimide were added thereto, and the resultant was aged for another 8 hours.

Then, a low-boiling component of the thus obtained crude liquid was removed with an evaporator, and the resultant was washed with methanol to obtain a pale yellow wet powder. The obtained wet powder was recrystallized with $CHCl_3/CH_3OH$ (70/30 (v/v)) to obtain 11.2 g of 1,2,4,5-cyclohexanetetracarboxylic acid di(2-ethylhexylamide) di(stearylamide) [a mixture of 1,2,4,5-cyclohexanetetracarboxylic acid-1,4-di(2-ethylhexylamide)-2,5-di(stearylamide) and 1,2,4,5-cyclohexanetetracarboxylic acid-1,5-di(2-ethylhexylamide)-2,4-di(stearylamide)] (yield: 57%). The structure of the thus obtained reaction product was analyzed by $^1$H-NMR.

$^1$H-NMR (270 MHz, $CDCl_3$): δ0.81-0.88 (m, 18H), 1.0-1.4 (m, 84H), 1.40-1.45 (m, 2H), 2.57-2.77 (m, 8H), 2.85-3.12 (m, 4H), 6.31 (s, 4H)

Comparative Example 1 [Synthesis of
Thickening/Stabilizing Agent (3)
(1,2,3-propanetricarboxylic Acid
tris(2-methylcyclohexylamide))]

A 100 mL four-necked separable flask equipped with a Dimroth condenser, a nitrogen inlet, a dropping funnel and a thermocouple was charged with 20 mL of pyridine, 2.97 g (0.017 mol) of 1,2,3-propanetricarboxylic acid, and 7.0 g (0.056 mol) of diisopropylcarbodiimide, and the resultant was aged for 3 hours with a temperature within the system set to 50° C.

Thereafter, 5.7 g (0.051 mol) of 2-methylcyclohexylamine was added thereto, and the resultant was aged for another 8 hours.

Then, a low-boiling component of the thus obtained crude liquid was removed with an evaporator, and the resultant was washed with methanol to obtain a pale yellow wet powder. The thus obtained wet powder was washed with acetone to obtain 4.7 g of 1,2,3-propanetricarboxylic acid tris(2-methylcyclohexylamide) (yield: 61%).

Examples 3 and 4 and Comparative Example 2

Each of fluid organic substances (liquid paraffin, isododecane and cetyl octanoate: all having a boiling point of not less than 100° C.) shown in Table 1 was weighed in a test tube in an amount of 1 cm³, 10 mg of the thickening/stabilizing agent obtained in each of Examples 1 and 2 and Comparative Example 1 described above was added thereto to be mixed, and the resultant was heated at 100° C. under stirring for compatibilizing the fluid organic substance and the thickening/stabilizing agent, and then was cooled to 25° C. to obtain a thickened/stabilized composition.

The viscosity of the thus obtained thickened/stabilized composition was measured to find how many times the viscosity of each of the fluid organic substances was increased, so as to evaluate the thickening property on the basis of the following criteria, and the thickening effect was determined as good if all the evaluation results of the thickening properties against these solvents are scores of not less than 4, and determined as poor if the evaluation results of the thickening properties against these solvents include a score of not more than 3.

<Evaluation Criteria>

1: The viscosity was increased by a factor of more than 1.0 and not more than 2.0.
2: The viscosity was increased by a factor of more than 2.0 and not more than 4.8.
3: The viscosity was increased by a factor of more than 4.8 and not more than 10.
4: The viscosity was increased by a factor of more than 10 and not more than 50.
5: The viscosity was increased by a factor of more than 50 and not more than 100.
6: The viscosity was increased by a factor of more than 100 and not more than 10000.

The viscosities of the various fluid organic substances and the thickened/stabilized compositions were measured as follows: A viscosity/viscoelasticity measuring apparatus (rheometer) (product name "RheoStress 600", manufactured by HAAKE) equipped with a cone-plate sensor (having a diameter of 60 mm and a cone angle of 1 degree or a diameter of 35 mm and a cone angle of 1, 2 or 4 degrees) and a Peltier temperature controller was used to obtain a viscosity curve by measuring viscosities at 25° C. in a normal flow viscosity measurement mode with a shearing velocity changed in logarithmic increments from 0.001 to 100 (1/s), and a viscosity at a shearing velocity of 10 (1/s) on the obtained viscosity curve was defined as the viscosity of the present invention. It is noted that a value obtained when the torque fluctuation of the measurement apparatus was within 5% and the data had become stable was employed for plotting each point.

The results are shown in a table below.

TABLE 1

|  |  | Example 3 Thickening/ stabilizing Agent (1) | Example 4 Thickening/ stabilizing Agent (2) | Comparative Example 2 Thickening/ stabilizing Agent (3) |
|---|---|---|---|---|
| Fluid Organic Substance | Liquid Paraffin | 6 | 6 | — |
|  | Isododecane | 6 | 6 | — |
|  | Cetyl Octanoate | 4 | 5 | — |
| Thickening Effect |  | Good | Good | Poor |

Note: In Comparative Example 2, the thickening/stabilizing agent (3) was not dissolved in any of the fluid organic substances, and showed no thickening effect.

Thus, it is understood that the thickening/stabilizing agent of the present invention is excellent in the effect of thickening a fluid organic substance.

INDUSTRIAL APPLICABILITY

A compound of the present invention represented by formula (1) can easily thicken or gel a fluid organic substance or homogeneously stabilize a composition containing a fluid organic substance when compatibilized with the fluid organic substance. Therefore, if it is used in a cosmetic product, a coating, food, a drug or the like, the viscosity of the resultant can be adjusted to a desired range, the constitution of the resultant can be uniformly retained, and the usability of the resultant can be improved.

The invention claimed is:

1. A compound represented by the following formula (1):

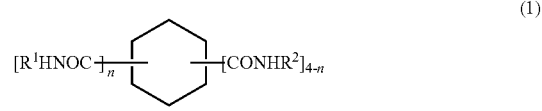

wherein
  $R^1$ represents straight chain or branched chain alkyl groups having 6 to 20 carbon atoms,
  $R^2$ represents straight chain or branched chain alkyl groups, alkenyl groups, or alkynyl groups having not less than 6 carbon atoms,
  $R^1$ and $R^2$ are different from each other, and
  n represents an integer of 1 to 3.

2. A thickening/stabilizing agent comprising
  one compound according to claim 1 or two or more different compounds according to claim 1; and
  at least one additional component.

3. A thickened/stabilized composition comprising the thickening/stabilizing agent according to claim 2 and a fluid organic substance.

4. A method for producing a thickened/stabilized composition, wherein a thickened/stabilized composition is obtained through a step of
compatibilizing the thickening/stabilizing agent according to claim 2 and a fluid organic substance.

5. The thickening/stabilizing agent of claim 2, wherein the total content of said compound or compounds is not less than 0.5% by weight in said thickening/stabilizing agent.

6. The thickening/stabilizing agent of claim 5, wherein the total content of said compound or compounds is not less than 85% by weight in said thickening/stabilizing agent.

7. The compound of claim 1, wherein $R^1$ is ethylhexyl, $R^2$ is oleyl, and n is 2, said compound being
1,2,4,5-cyclohexanetetracarboxylic acid di(2-ethylhexylamide) di(oleylamide).

8. The compound of claim 1, wherein $R^1$ is ethylhexyl, $R^2$ is stearyl, and n is 2, said compound being
1,2,4,5-cyclohexanetetracarboxylic acid di(2-ethylhexylamide) di(stearylamide).

9. The thickening/stabilizing agent according to claim 2, wherein said at least one additional component comprises a base, a hydroxy fatty acid, an acrylic polymer, an oligomer ester, or metal oxide particles.

\* \* \* \* \*